United States Patent [19]

Hardtmann

[11] 3,963,720

[45] June 15, 1976

[54] TETRACYCLIC IMIDAZO [2,1-b] QUINAZOLINONE DERIVATIVES

[75] Inventor: Goetz E. Hardtmann, Florham Park, N.J.

[73] Assignee: Sandoz, Inc., E. Hanover, N.J.

[22] Filed: June 21, 1974

[21] Appl. No.: 481,698

Related U.S. Application Data

[63] Continuation-in-part of Ser. No. 301,648, Oct. 27, 1972.

[52] U.S. Cl. .......................... 260/256.4 F; 424/251
[51] Int. Cl.[2].............. C07D 471/04; C07D 487/04
[58] Field of Search.............................. 260/256.4 F

[56] References Cited
UNITED STATES PATENTS 3,669,969  1/1972  Lunn ........................... 260/256.4 F

*Primary Examiner*—Raymond V. Rush
*Assistant Examiner*—James H. Turnipseed
*Attorney, Agent, or Firm*—Gerald D. Sharkin; Richard E. Vila

[57] ABSTRACT

Disclosed are compounds which are tetracyclic derivatives of imidazo[2,1-b]quinazolinones, e.g., 6-(p-fluorobenzyl)-1,2,3,4,4a,12a-hexahydrobenzimidazo[2,1-b]quinazolin-11(6H)-one. The compounds are also useful as bronchodilator agents, and certain compounds are also useful as tranquillizers and sedative/hypnotic agents. The compounds may be prepared by reacting an isatoic anhydride with a 2-organomercapto-hexahydrobenzimidazole or hexahydrocyclopentimidazole such as 3a,4,5,6,7,7a-hexahydro-2-mercaptomethyl-3H-benzimidazole.

18 Claims, No Drawings

TETRACYCLIC IMIDAZO [2,1-b] QUINAZOLINONE DERIVATIVES

This application is a continuation-in-part of copending now abandoned application Ser. No. 301,648, filed Oct. 27, 1972.

The present invention relates to tetracyclic chemical compounds which are derivatives of imadazo[2,1-b]quinolinones, to their preparation and intermediates useful in their preparation and to pharmaceutical methods and compositions utilizing the pharmacological properties of said compounds.

The compounds of the present invention may be represented structurally by the following formula I:

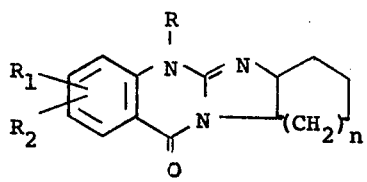

wherein
R is alkyl of 1 to 8 carbon atoms, alkenyl of 3 to 10 carbon atoms, e.g., allyl, methallyl, crotyl, hexene-5 and octene-7; alkynyl of 3 to 6 carbon atoms, e.g., propargyl, or

n is 0 or 1;
A is a direct bond or straight chain or branch alkylene of 1 to 3 carbon atoms,
each of $R_1$ and $R_2$ is, independently, hydrogen, halo of atomic weight not greater than 36, lower alkyl of 1 to 3 carbon atoms or lower alkoxy of 1 to 2 carbon atoms; or one is hydrogen and the other bromo or trifluoromethyl, and
each of Y and Y' is, independently, hydrogen, halo of atomic weight not greater than 36, i.e. fluoro or chloro, lower alkyl of 1 to 3 carbon atoms or lower alkoxy of 1 to 2 carbon atoms, or one is hydrogen and the other bromo or trifluoromethyl,
or a pharmaceutically acceptable acid addition salt thereof.

The generally preferred method for preparation of compounds of formula I involves reacting in a Step A a compound of the formula II:

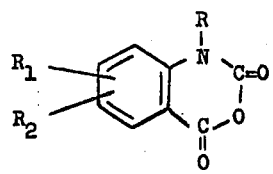

where $R_1$, $R_2$ and R are as defined, with a compound of formula III:

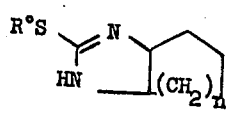

wherein n is as defined and R° is lower alkyl of preferably 1 to 4 carbon atoms or benzyl.

The preparation of compounds I by the reaction of Step A can be carried out at temperatures in the range of 20°C. to 160°C., more usually 20°C. to 140°C., preferably 80°C. to 120°C. The reaction is conveniently carried out in an organic solvent of conventional type providing an inert reaction medium. The aromatic solvents and cyclic ethers suitable for use at reflux temperatures represent the preferred solvents, e.g. toluene and dioxane. The reaction is preferably carried out in the presence of a base, e.g. sodium hydroxide or sodium carbonate; and when the compound III is employed directly in acid addition salt form, it is of course desirable to employ an amount of base somewhat greater than the amount necessary to neutralize the acid. In general, the reaction product of formula I may be recovered from the reaction of Step A by working up by conventional procedures.

The compounds of the formula II are either known or may be prepared from known materials by known methods. The compounds of the formula III may be prepared by reacting in a Step 1 a compound of the formula IV:

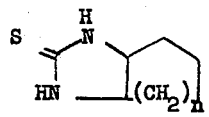

wherein n is as defined, with an organic halide of the formula V:

XR°      V wherein R° is as defined and X is halo of atomic weight of from 35 to 130.

The preparation of compound III by Step 1 involving the reaction of a compound IV with a compound V may be suitably carried out at temperatures in the range of 10°C. to 100°C., preferably 20°C. to 80°C. The reaction is carried out in an organic solvent which may be any of several conventional solvents providing an inert reaction medium. The more suitable solvents include, for example, the ethers and lower alkanols, e.g., ethanol or methanol. The compounds of the formula III may be conveniently first produced in acid addition salt form and converted to free base form as desired. The reaction product of formula III in free base or acid addition salt form may be recovered from Step 1 by working up by established procedures.

The compounds of the formula IV may be prepared by reacting in a Step 2 reaction a compound of the formula VI:

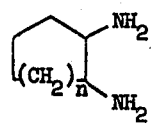

wherein n is as defined, with carbon disulfide.

The preparation of compounds IV by the reaction of Step 2 involving the reaction of a compound VI with carbon disulfide is suitably carried out at temperatures in the range of 30°C. to 140°C., preferably 50°C. to 100°C. The reaction is carried out in an organic solvent of which several of known type may be employed such as the lower alcohols, e.g. ethanol. The reaction product of formula IV may be recovered from Step 2 by working up by known procedures.

The compounds of formula VI employed as starting material in the reaction of Step 2 are known or may be readily provided from available materials as described in the literature.

Also within the scope of the novel compounds provided by the invention are pharmaceutically acceptable salts not materially depreciating the pharmacological effect of the compounds. Such salts include the acid addition salts of known type, e.g. the hydrochloride. The acid addition salts may be produced from the corresponding free bases by conventional procedures. Conversely, the free bases may be obtained from the salts by procedures known in the art.

The compounds of formula I of the invention are useful because they possess biological activity. In particular, the compounds of the formula I are useful as bronchodilator agents as indicated by measuring bronchial resistance on intravenous administration (0.1 – 5 mg./kg.) in the anesthetized guinea pig according to the test of Konzett and Tossler, Arch. Exp. Path. und Pharmak. 195 : 71 (1940); and by observing the respiratory status on oral administration (0.5 – 100 mg./kg.) to the unanesthetized guinea pig exposed to aerosolized histamine dihydrochloride according to a modification of the method of Van Arman et al. J. Pharmacol. Exptl. Therap. 133: 90–97, 1961; and in vitro by observing the effect (0.1 – 30 micrograms/ml.) on strips of guinea pig trachea according to the method of Constantine, J. Pharm. Pharmacol. 17: 384–385, 1960. For such use and depending upon known variables satisfactory results are obtained in general on the daily administration of from 0.4 to 100 milligrams per kilogram of body weight, preferably given in divided doses to 2 to 4 times a day, or in sustained release form. For most mammals the administration of from 24 to 3000 milligrams per day provides satisfactory results and dosage forms suitable for internal administration comprise 6 to 1500 milligrams of the compound in admixture with a solid or liquid pharmaceutical carrier or diluent.

The preferred compounds of the invention from the standpoint of bronchodilator activity are those in which R is benzyl including substituted benzyl, particularly unsubstituted benzyl and halobenzyl, e.g. fluorobenzyl, more particularly 4-halobenzyl, and the more preferred compounds are those in which each of $R_1$ and $R_2$ is hydrogen.

The compounds of formula I in which R is alkyl of 1 to 8 carbon atoms or phenyl (including substituted phenyl) also effect a depression of the central nervous system and are useful as minor tranquilizers and sedative/hypnotic agents as indicated by their ability to produce docility in behavior tests in mice given 10 to 200 mg./kg. i.p. of test compound according to the 30-word adjective check sheet system, basically described by S. Irwin, Gordon Research Conference, Medicinal Chemistry, 1949 and Chem. Symposium on Sedative and Hypnotic Drugs, Williams and Wilkins, 1954, by effecting a reinduction of hexobarbital anesthesia in mice (10 to 200 mg./kg.) according to the method of Winter, J. Pharmacol. and Exp. Therap., 94, 7–11, 1948, and by inducing sleep in sleep studies in cats in which the various stages of sleep are monitored by chronically implanted electrodes and the results compared with controls. For such uses, the compounds may be administered orally or parenterally, preferably orally, and in admixture with conventional pharmaceutical carriers. The dosage administered may vary depending upon known variables such as the particular compound employed, the treatment desired and the severity of the conditions being treated. In general, satisfactory results are obtained when administered at a daily dosage of from about 2 milligrams to about 150 milligrams per kilogram of animal body weight, preferably given orally and in a single dose at bedtime for sedative/hypnotic use, or in divided doses 2 to 4 times a day for use as tranquilizers. For most mammals, the administration of from about 160 milligrams to about 1600 milligrams of the compound per day provides satisfactory results with a single dose of from 160 to 1600 milligrams, preferably 160 to 800 milligrams, being given at bedtime for sedative/hypnotic use. For use as tranquilizers, the compounds of formula I are given in divided doses of from 40 to 800 milligrams, preferably 40 to 400 milligrams, 2 to 4 times a day. The compounds of formula I are suitably administered in admixture with a solid or liquid pharmaceutically acceptable carrier or diluent.

For the uses indicated above, the compounds may be combined with a pharmaceutically acceptable carrier, and such other conventional adjuvants as may be necessary, and adminstered orally or parenterally. For most uses oral administration with carriers is preferred and may take place in such conventional formas as tablets, dispersible powders, granules, capsules, suspensions syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred phaarmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for prophylatic treatment of bronchial asthma and prepared by conventional tabletting techniques to contain the following ingredients:

| Ingredients | Weight (mg.) |
|---|---|
| 6-(4'-fluorobenzyl)-1,2,3,4,4a,12a-hexahydrobenzimidazo[2,1-b]quinazolin-11(6H)-one | 25 |
| Tragacanth | 10 |
| Lactose | 222.5 |
| Corn Starch | 25 |
| Talcum | 15 |
| Magnesium Stearate | 2.5 |

In addition, the compounds of the formula I may be administered as bronchodilators by inhalation therapy in a conventional manner, e.g., by the use of nebulizers, vaporizers, aerosols and the like. Compositions for use in administration by inhalation therapy may be prepared according to conventional procedures and contain the usual conventional ingredients employed in such compositions. A representative aerosol formulation prepared by conventional techniques for use with a metered value system contains the following ingredients:

| | |
|---|---|
| 6-(4'-fluorobenzyl)-1,2,3,4,4a,12a-hexahydrobenzimidazo[2,1-b]quinazolin-11(6H)-one | 0.4–20% |
| Ethyl alcohol | 10–40% |
| Ascorbic Acid | 1–10% |
| Freon 11 | 10–30% |
| Freon 114 | 10–30% |
| Freon 12 | 30–60% |
| Buffer System - pH control | q.s. |
| Flavor | q.s. |

Two capsules each containing the following ingredients and prepared by conventional techniques are contemplated as suitable for administration at bedtime for sedative/hypnotic use:

| Ingredient | Weight (mg.) |
|---|---|
| 6-methyl-1,2,3,4,4a,12a-hexahydrobenzimidazo 2,1-b quinazolin-11(6H)-one | 100 |
| Kaolin | 250 |

The following examples show representative compounds encompassed within the scope of this invention and the manner in which such compounds are prepared. However, it is to be understood that the examples are for purposes of illustration only.

EXAMPLE A 3a,4,5,6,7,7a-hexahydro-2-mercaptomethyl-3H-benzimidazole

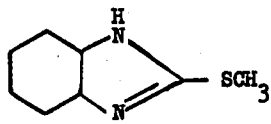

STEP A: To a mixture of 67 g. of carbon disulfide in 300 ml. of ethanol is added dropwise with stirring a solution of 100 g. of 1,2-diaminocyclohexane in 100 ml. of ethanol. The resulting solution is stirred one-half hour after addition; liquid eliminated and the residue dissolved in 300 ml. of water and heated at reflux for 18 hours. The precipitate which forms on cooling is filtered off, washed with water and then with ether and dried under reduced pressure to obtain 3a,4,5,6,7,7a-hexahydro-2-benzimidazolin-thione, m.p. 170°C.

STEP B: To a suspension of 53 g. of 3a,4,5,6,7,7a-hexahydro-2-benzimidazolin-thione in 150 ml. of ethanol is added 49 g. of methyl iodide. After shaking a solution forms which is allowed to stand at ambient temperature for 16 hours. A small amount of pentane is then added and the solution cooled to obtain a precipitate which is filtered off, washed with pentane and dried under reduced pressure to obtain 3a,4,5,6,7,7a-hexahydro-2-mercaptomethyl-3H-benzimidazole hydroiodide, m.p. 180°–184°C. A solution of 20 g. of the acid addition salt in 200 ml. of water is cooled in an ice bath and 6.5 g. of sodium hydroxide in a 50% aqueous solution is added dropwise followed by stirring for 2 hours. The solution is extracted twice with methylene chloride, the combined extracts dried, evaporated in vacuo and pentane added to obtain a precipitate which is recovered by filtering, washed with pentane and dried under reduced pressure to obtain 3a,4,5,6,7,7a-hexahydro-2-mercaptomethyl-3H-benzimidazole, m.p. 125°–129°C.

EXAMPLE B

Following the procedures of Example A the following are obtained:
a. 1,3a,4,5,6,6a-hexahydro-2-cyclopentimidazolin-thione.
b. 1,3a,4,5,6,6a-hexahydro-2-mercaptomethyl-3H-cyclopentimidazole.
c. 3a,4,5,6,7,7a-hexahydro-2-mercaptobenzyl-3H-benzimidazole.

EXAMPLE 1

6-(4'-fluorobenzyl)-1,2,3,4,4a,12a-hexahydrobenzimidazo[2,1-b]quinazolin-11(6H)-one.

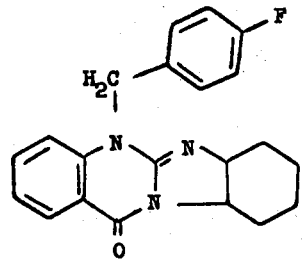

A suspension of 6 g. of 3a,4,5,6,7,7a-hexahydro-2-mercaptomethyl-3H-benzimidazole, 10 g. of N-(p-fluorobenzyl)isatoic anhydride and 1 pellet of sodium hydroxide in 170 ml. of dioxane is refluxed for 5.5 hours, the solvent evaporated off, the residue dissolved in chloroform followed by extraction with water which extract is discarded and then extraction 3 times with 1N. hydrochloric acid solution. The combined acidic extracts are filtered and treated with sodium carbonate solution. After 2 hours a precipitate is formed and filtered off, washed with water, and crystallized from methylene chloride/ether to obtain solids which are dried under reduced pressure to obtain the heading compound, m.p. 186°–191°C. The chloroform solution is treated with shaking with sodium carbonate, dried, and filtered through silica gel followed by crystallization from methylene chloride/ether and drying under reduced pressure to obtain additional quantities of the heading compound, m.p. 196°–199°C.

EXAMPLE 2

Following the procedure of Example 1 the following compounds of the invention are obtained:

a. 6-benzyl-1,2,3,4,4a,12a-hexahydrobenzimidazo[2,1-b]quinazolin-11(6H)-one.
b. 6-ethyl-1,2,3,4,4a,12a-hexahydrobenzimidazo[2,1-b]quinazolin-11(6H)-one.
c. 6-benzyl-9-chloro-1,2,3,4,4a,12a-hexahydrobenzimidazo[2,1-b]quinazolin-11(6H)-one.
d. 6-(5-hexenyl)-1,2,3,4,4a,12a-hexahydrobenzimidazo[2,1-b]quinazolin-11(6H)-one.
e. 6-allyl-1,2,3,4,4a,12a-hexahydrobenzimidazo[2,1-b]quinazolin-11(6H)-one.
f. 6-propargyl-1,2,3,4,4a,12a-hexahydrobenzimidazo[2,1-b]quinazolin-11(6H)-one.
g. 6-phenethyl-1,2,3,4,4a,12a-hexahydrobenzimidazo[2,1-b]quinazolin-11(6H)-one.
h. 5-(4'-fluorobenzyl)-1,2,3,3a,11a-tetrahydro-1H-cyclopentimidazo[2,1-b]quinazolin-10(5H)-one.
i. 5-benzyl-2,3,3a,11a-tetrahydro-1H-cyclopentimidazo[2,1-b]quinazolin-10(5H)-one.
j. 6-methyl-1,2,3,4,4a,12a-hexahydrobenzimidazo[2,1-b]quinazolin-11(6H)-one, m.p. 167°–170°C.
k. 5-methyl-2,3,3a,11a-tetrahydro-1H-cyclopentimidazo[2,1-b]quinazolin-10(5H)-one.
l. 6-phenyl-1,2,3,4,4a,12a-hexahydrobenzimidazo[2,1-b]quinazolin-11(6H)-one.
m. 5-phenyl-2,3,3a,11a-tetrahydro-1H-cyclopentimidazo[2,1-b]quinazolin-10(5H)-one.
n. 9-chloro-6-methyl-1,2,3,4,4a,12a-hexahydrobenzimidazo[2,1-b]quinazolin-11(6H)-one.

What is claimed is:

1. A compound of the formula:

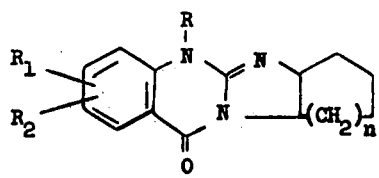

wherein
R is alkyl of 1 to 8 carbon atoms, alkenyl of 3 to 10 carbon atoms, alkynyl of 3 to 6 carbon atoms or

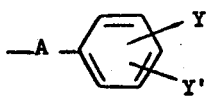

$n$ is 0 or 1,
A is a direct bond or a straight chain or branched alkylene of 1 to 3 carbon atoms;

each of $R_1$ and $R_2$ is, independently, hydrogen, halo of atomic weight not greater than 36, alkyl of 1 to 3 carbon atoms or alkoxy of 1 to 2 carbon atoms; or one is hydrogen and the other bromo or trifluoromethyl, and each of Y and Y' is, independently, hydrogen, halo of atomic weight not greater than 36, alkyl of 1 to 3 carbon atoms or alkoxy of 1 to 2 carbon atoms, or one is hydrogen and the other bromo or trifluoromethyl;

or a pharmaceutically acceptable acid addition salt thereof.

2. A compound of claim 1 in which R is alkyl.
3. A compound of claim 1 in which R is alkenyl.
4. A compound of claim 1 in which R is alkynyl.
5. A compound of claim 1 in which R is

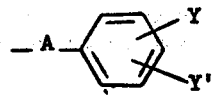

wherein A is alkylene.

6. A compound of claim 1 in which $n$ is 0.
7. A compound of claim 1 in which $n$ is 1.
8. A compound of claim 5 in which $n$ is 0.
9. A compound of claim 8 in which A is methylene.
10. A compound of claim 9 in which $R_1$ and $R_2$ are hydrogen, Y is hydrogen or halo and Y' is hydrogen.
11. The compound of claim 10 in which Y is hydrogen.
12. The compound of claim 10 in which Y is para-fluoro.
13. A compound of claim 1 in which R is

14. A compound of claim 2 in which R is alkyl of 1 to 3 carbon atoms.
15. A compound of claim 14 in which R is methyl.
16. The compound of claim 15 in which n is 1 and each of $R_1$ and $R_2$ is hydrogen.
17. A compound of claim 1 in which R is alkyl or

18. A compound of claim 14 in which R is ethyl.

* * * * *